United States Patent [19]

Blay

[11] 4,075,700
[45] Feb. 21, 1978

[54] INFORMATION DISPLAY ARRANGEMENTS

[75] Inventor: Alan George Blay, Kenley, England

[73] Assignee: EMI Limited, Hayes, England

[21] Appl. No.: 703,004

[22] Filed: July 6, 1976

[30] Foreign Application Priority Data

July 4, 1975 United Kingdom ............... 28219/75

[51] Int. Cl.$^2$ .................. G01T 1/16; G08C 21/00
[52] U.S. Cl. ................................. 364/515; 364/413; 250/336; 340/324 A
[58] Field of Search .................... 235/151.3; 250/362, 250/363 R, 336, 369, 455 T; 178/DIG. 5, DIG. 22; 340/324 A, 324 AD

[56] References Cited

U.S. PATENT DOCUMENTS

| | | | |
|---|---|---|---|
| 3,389,404 | 6/1968 | Koster | 340/324 A X |
| 3,736,564 | 5/1973 | Watkins | 340/324 A X |
| 3,778,614 | 12/1973 | Hounsfield | 178/DIG. 5 X |
| 3,813,545 | 5/1974 | Barnhart et al. | 250/306 |
| 3,832,693 | 8/1974 | Ishizaki et al. | 340/324 A X |
| 3,924,129 | 12/1975 | LeMay | 250/336 |
| 3,936,636 | 2/1976 | Percival | 250/336 |
| 3,944,988 | 3/1976 | Mayer | 340/324 A X |

Primary Examiner—Edward J. Wise
Attorney, Agent, or Firm—Cooper, Dunham, Clark, Griffin & Moran

[57] ABSTRACT

The data derived from a computerized axial tomographic apparatus in respect of a number of slices through a body are processed to produce a representation of the variation of absorption of X-rays over each slice. The representations are operated upon individually to identify areas which are of reduced interest and/or which are obscuring regions of especial interest. This having been done, the representations for all the slices are correlated to produce a pseudo three-dimensional display of part of the body with the identified areas being displayed with reduced or zero intensity as compared with other areas. Alternatively, the identified and other areas can be represented in different colors.

5 Claims, 1 Drawing Figure

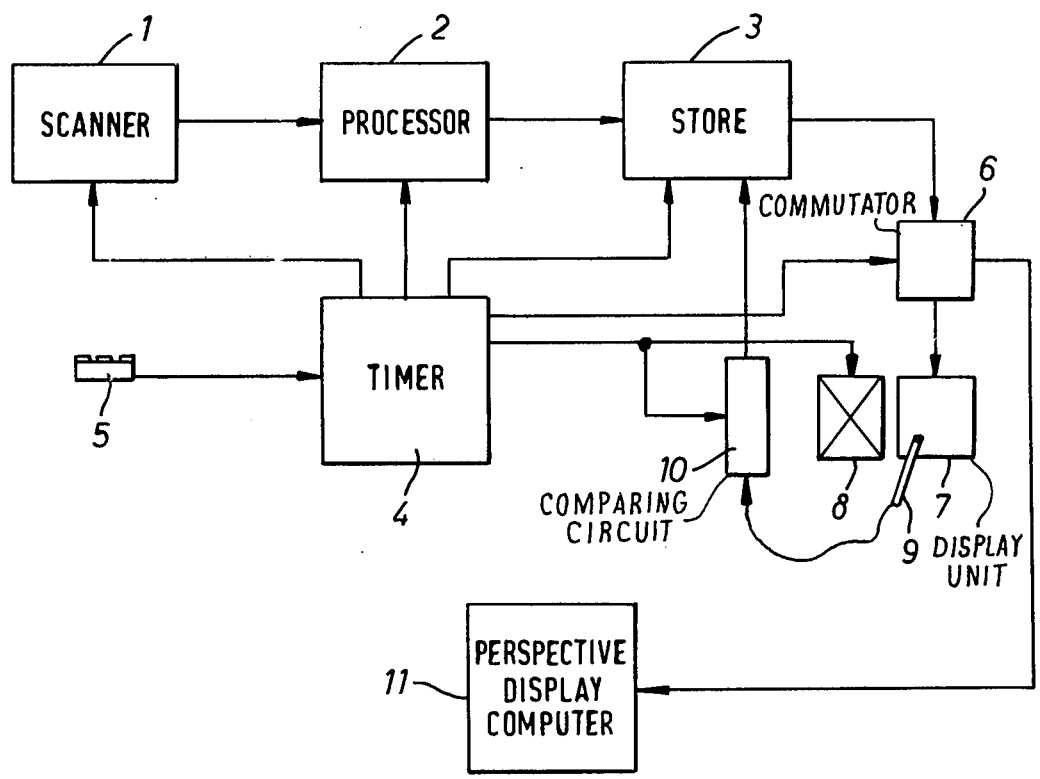

INFORMATION DISPLAY ARRANGEMENTS

The present invention relates to information display arrangements, and it relates especially, though not exclusively, to the display of information indicative of the distribution of absorption coefficients, with respect to penetrating radiation such as X- or γ-radiation, or ultrasonic waves, across a planar slice of finite thickness cross-sectionally disposed in a body. Such information can be obtained, for example, by means of the apparatus described in U.S. Pat. No. 3,778,614.

It is the practice to obtain such information in respect of several adjacent, and substantially parallel, slices through the body and it is also possible to synthesize similar information in respect of additional slices, between adjacent pairs of said several slices, by a process of interpolation.

Whether or not the aforementioned interpolation is carried out, information relating to several of said slices is available, and since the slices are spaced apart in a direction perpendicular to their planes it is possible to build up a three-dimensional representation of the absorption coefficients of the body.

If such a three-dimensional display is constructed, however, a difficulty arises in that certain features of interest may be partially or completely obscured form view by matter which is not of interest. It is an object of this invention to provide an information display arrangement which takes advantage of the availability of the requisite information to construct a three-dimensional representation of said absorption coefficients and which includes means whereby the difficulty referred to above is mitigated.

According to the invention, there is provided an information display arrangement including a store for information signals indicative of variation of a parameter of a body over each of a plurality of substantially two-dimensional regions in the body, adjacent regions overlying one another to at least a substantial extent, means for displaying individually the information signals relating to at least some of said regions, means for selecting features of interest contained in the displayed information, and means for combining the information so displayed to provide a pseudo three-dimensional display of part of said body with the selected features shown in relief.

In order that the invention may be clearly understood and readily carried into effect, one embodiment thereof will now be described, by way of example only, with reference to the accompanying drawing the single FIGURE of which represents, in block diagrammatic form, an arrangement in accordance with one example of the invention.

Referring now to the drawing, a scanner 1, for example of the kind described in the aforementioned U.S. Pat. No. 3,778,614 or alternatively of other suitable kind, is arranged to irradiate a body (not shown) along a plurality of paths in each of a number of substantially parallel planes and to provide output signals indicative of the absorption suffered by the radiation on traversing each of said paths. The output signals are digitised and converted to logarithmic form and are passed to a digital processing circuit 2, which may be, for example, of the kind described in U.S. Pat. No. 3,924,129. The circuit 2 provides an indication of the absorption coefficient, with respect to the radiation used, for the elements of a two-dimensional array of elements notionally set out in each of said planes. The evaluated coefficients are passed to a digital store 3 wherein they are held in respective storage locations. The operations of the scanner 1, the processing circuits 2 and the store 3 are all carried out under the control of a master timing circuit 4, which also responds to a manually generated command signal from a starting unit 5 to initiate the cycle of operation to be carried out by components 1 to 3.

The store 3 is coupled to a commutating arrangement 6, which is operated under the control of the master timing circuit 4 to connect the store 3 to a cathode ray tube display unit 7, arranged to display the coefficients relating to a chosen slice in two-dimensional form in television raster format. Associated with the unit 7 are scanning coils, schematically indicated at 8, which are supplied with deflection waveforms from the master timing circuit 4.

A light pen 9 is provided in order to permit the generation of signals indicative of the position co-ordinates on the display unit 7 of features in the slices which are not of interest and/or which are obscuring, at least in part, a feature of special interest in said slice. This is achieved by pointing the light pen at said first mentioned features, or by effectively drawing a boundary around them. The pen 9 produces signals when the scanning spot of the cathode ray tube passes the part of the screen at which the pen is pointed. The time at which such signals are generated in relation to the stage in the scanning reached is indicative of the position co-ordinates of the aforementioned part of the screen. The signals provided by pen 9 are compared with the deflection waveforms in a circuit 10 to derive the aforementioned position co-ordinates which are applied to the store 3 which is then effective to associate coded label signals with the stored values relating to the delineated features. By subsequently feeding a signal to the store 3 which instruct that all labelled features be attributed zero or maximum absorption coefficient, it will be seen that matter of little interest can effectively be "erased".

In an alternative arrangement, the light pen 9 may be used to "draw" a line which closely surrounds a feature of special interest and the store 3 may be arranged to respond by associating "erasing" labels with all information relating to features outside said line thus leaving, in effect, a representation which only includes the delineated feature.

Instead of causing the erasure of labelled features, they may be displayed with lower intensity than, and/or in a different colour to, unlabelled features. In any event, the latter features are displayed in relief.

It will be appreciated that (ignoring any interpolated information which may be provided) the store 3 holds, in respective storage levels, the evaluated absorption coefficients relating to a number of said slices, for example eight slices may be investigated. The stored information relating to each slice is applied in turn at a rate which is controllable by an operator, via the handset 5, to the display unit 7 and each representation displayed thereon is (so far as is necessary) operated upon with the light pen 9 to cause the relevant storage locations in store 3 to associate the aforementioned labels with selected features of the information stored therein.

After this procedure has been completed, the store 3 holds eight sets of absorption coefficients, some of which will have labels associated therewith, and the timing unit 4 is arranged to switch over the commutating arrangement 6 to couple the store 3 to a special purpose digital computer 11 which is arranged to accept the eight sets of absorption values from store 3 and to operate on them to produce a two-dimensional display with perspective in a manner known per se. This perspective display thus provides, in effect, a pseudo three-dimensional view of the section of the body which contains all eight of said slices. In accordance with the invention, however, matter which is of interest stands in relief of matter which is not of interest and/or which obscures partially or totally, a feature of special interest. This enables an operator viewing the display to obtain a good view of, and to concentrate upon, features of special interest.

Various modifications of the arrangement described may be effected without departing from the scope of the invention. For example the light pen 9 can be arranged so that the line or lines "drawn" to divide matter of interest and other matter are spatially smoothed so as to avoid the production of sharp transitions between "erased" and "non erased" portions of the representation.

It will be appreciated that if absorption coefficients are "erased" from locations in each slice which are identical to one another or are correlated in a predetermined way, the effect can be achieved of making a cut through successive slices so as to render visible the features lying in a selected cross-section through the slices. Alternatively portions of successive slices may be "erased" so as to reveal the absorption values at the intersecting surfaces.

It is also of value, in some circumstances, to selectively cut back through a chosen position of the total number of layers, thereby revealing intersecting surfaces through features of interest.

Instead of using a light pen, as described hereinbefore, a tracker ball or joystick arrangement of known kind can be used.

What I claim is:

1. An information display arrangement including a store for information signals indicative of variation of a parameter of a body over each of a plurality of substantially two-dimensional regions in the body, adjacent regions overlying one another to at least a substantial extent, means for displaying individually the information signals relating to at least some of said regions, means for selecting features of interest contained in the displayed information, and means for combining the information so displayed to provide a pseudo three-dimensional display of part of said body with the selected features shown in relief.

2. An arrangement according to claim 1 wherein said means for selecting comprises means for delineating features other than said features of interest and for feeding to the store label signals for association with the parameter values stored for said other features.

3. An arrangement according to claim 2 wherein said means for combining comprises perspective display computer means adapted to respond to said label signals to effect said relief.

4. An arrangement according to claim 2 wherein said delineating means comprises a light pen and associated circuits.

5. A method of displaying information comprising the steps of:

storing information signals indicative of variation of a parameter of a body over each of a plurality of substantially two-dimensional regions in the body, adjacent regions overlying one another to at least a substantial extent; displaying individually the information signals relating to at least some of said regions; selecting features of interest contained in the displayed information relating to said at least some regions; and combining the information so displayed to provide a pseudo three-dimensional display of part of said body with the delineated features shown in relief.

* * * * *